United States Patent [19]

Duranleau et al.

[11] 4,028,388

[45] June 7, 1977

[54] PREPARATION OF ACIDS

[75] Inventors: Roger G. Duranleau, Ardonia; John M. Larkin, Wappingers Falls, both of N.Y.

[73] Assignee: Texaco Inc., New York, N.Y.

[22] Filed: Jan. 8, 1976

[21] Appl. No.: 647,399

[52] U.S. Cl. .............................. 260/413; 260/540; 260/541; 423/470
[51] Int. Cl.² .................. C07C 53/22; C07C 53/08
[58] Field of Search ...... 260/413, 540, 541, 566 A; 423/470

[56] References Cited

UNITED STATES PATENTS

| 2,734,084 | 2/1956 | Doerner | 260/566 A |
| 2,908,697 | 10/1959 | Kaupp et al. | 260/413 |
| 3,458,582 | 7/1969 | Lachowicz et al. | 260/413 |
| 3,794,620 | 2/1974 | Baterman | 260/566 A |
| 3,960,953 | 6/1976 | Duranleau et al. | 260/566 A |

*Primary Examiner*—Winston A. Douglas
*Assistant Examiner*—P. E. Konopka
*Attorney, Agent, or Firm*—Thomas H. Whaley; Carl G. Ries; George J. Darsa

[57] ABSTRACT

A method of preparing carboxylic acids is provided by heating an acylhydroximyl halide in an aqueous medium at elevated temperatures.

20 Claims, No Drawings

PREPARATION OF ACIDS

BACKGROUND OF THE INVENTION

This invention relates to a novel method of preparing carboxylic acids and particularly to the preparation of carboxylic acids from acylhydroximyl halides.

Carboxylic acids can be prepared by contacting nitroketones with aqueous sodium hydroxide or refluxing in sodium acetate. This method requires isolation of the intermediate sodium carboxylate and acidification to convert the intermediate to the acid. In another method involving the refluxing of nitroketones in aqueous ammonium hydroxide, there results a mixture of carboxylic acids and amides. U.S. Pat. No. 3,415,856 describes a method of preparing carboxylic acids by contacting a nitroketone with water in the presence of an acid, such as the mineral acid, a hydrocarbon sulfonic acid or a haloacetic acid and where the method produces two distinct carboxylic acids. While yields of 60 and 70 mole percent of monocarboxylic acids are indicated as provided by the method, there still remains substantial room for improvement. We have now found a method whereby individual carboxylic acids can be produced, which method also provides as a valuable coproduct an ammonium halide.

It is therefore an object of this invention to provide a method for the preparation of carboxylic acids in high yields.

Another object of this invention is to provide a method for the preparation of carboxylic acids from acylhydroximyl halides.

Yet another object of this invention is to provide a method for converting acylhydroximyl halides to a carboxylic acid and an ammonium halide.

Other objects and advantages will become apparent from a reading of the following detailed description and examples.

SUMMARY OF THE INVENTION

Broadly, this invention contemplates a method of preparing a carboxylic acid which comprises heating an acylhydroximyl halide in an aqueous medium at a temperature of about 70° to 220° C. The method produces as by-products carbon dioxide and an ammonium halide.

Pursuant to this invention, the acylhydroximyl halide converted to the carboxylic acid corresponds to the formula:

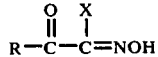

where R is an alkyl group having from 1 to 50 carbon atoms, suitably from 3 to 40 carbons and preferably 5 to 30 carbons, and where X is Cl, Br, I or F. Illustrative of the starting materials, we mention acetylhydroximyl chloride, acetylhydroximyl bromide, acetylhydroximyl iodide, acetylhydroximyl fluoride, propionylhydroximyl chloride, butanoylhydroximyl chloride, pentanoylhydroximyl chloride, pentanoylhydroximyl bromide, pentanoylhydroximyl iodide, pentanoylhydroximyl fluoride, hexanoylhydroximyl chloride, nonanoylhydroximyl chloride, undecanoylhydroximyl chloride, undecanoylhydroximyl bromide, undecanoylhydroximyl iodide, undecanoylhydroximyl fluoride, tetradecanoylhydroximyl chloride, pentadecanoylhydroximyl chloride, pentadecanoylhydroximyl bromide, pentadecanoylhydroximyl iodide, pentadecanoylhydroximyl fluoride, hexadecanoylhydroximyl chloride and eicosanoylhydroximyl chloride. Mixtures of acylhydroximyl halides as starting material are also contemplated and are converted to individual carboxylic acids or to mixtures of acids depending upon whether in the starting reactant R represents a uniform alkyl group or a range of mixture of alkyl groups. The acylhydroximyl halides contemplated as reactants herein can be prepared by the procedure described in our copending application Ser. No. 532,421 filed Dec. 12, 1974, now U.S. Pat. No. 3,960,953, issued June 1, 1976, which is herein incorporated by reference. Essentially the procedure in our copending application involves contacting a 1-nitro-2-alkanone having from 3 to 52 carbons with a halogen acid, such as hydrochloric acid, hydrobromic acid, hydroiodic acid or hydrofluoric acid in the presence of a polar protic organic solvent, such as a carboxylic acid or alcohol having from 2 to 16 carbon atoms illustrated by acetic acid, hexanoic acid, ethanol and butanol, at a temperature of from about 50° to 105° C. where the mole ratio of nitroketone to halogen acid to solvent is about 1:1:1 and 1:30:100. At the completion of this reaction, the product is essentially the desired acylhydroximyl halide which can be recovered by cooling the reaction mixture to below about 30° C. whereupon the acylhydroximyl halide crystallizes and is easily separated by filtration.

The method contemplated by this invention provides as the desired product a carboxylic acid of the formula:

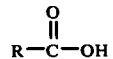

where by-products of the method are carbon dioxide ($CO_2$) and an ammonium ($NH_4X$) and where R and X are as heretofore defined. The carboxylic acid formed by the method possesses one carbon less than the starting acylhydroximyl halide and the conversion involves transformation of the halide through rearrangement and cleavage.

More specifically, the method of this invention comprises heating an acylhydroximyl halide as hereinabove defined or mixtures thereof in an aqueous medium at a temperature of from about 70° to 220° C., preferably 90° to 170° C. Temperatures below about 70° C. cause slow reaction and temperatures greater than about 220° C. cause substantial reduction in the desired product.

In accordance with out method, the acylhydroximyl halide is converted to a carboxylic acid by reacting with water at the temperatures recited above. To effect substantial conversion of the halide to the acid the reaction is conducted in the presence of at least greater than about five moles of water per mole of acylhydroximyl halide. In addition to functioning as a reactant, water can also be employed as the reaction medium in amounts up to about 200 parts by weight or higher of water per part by weight of acylhydroximyl halide. The method contemplated herein is generally conducted at a pH of about 0 to about 7, preferably between about 1 and 3, and can be assisted and the reaction time reduced by the additional presence of catalytic amounts of a mineral acid such as hydrochloric acid, sulfuric acid, nitric acid or phosphoric acid. Generally, the reaction time is between about one-quarter and 24 hours or longer.

The method also contemplates as an additional member of the aqueous medium, the use of an oxygenated polar organic solvent. The solvent employed should be sufficiently polar to permit the rearrangement reaction to occur and is further characterized as being capable of solubilizing the acrylhydroximyl halide reactant, water and ammonium halide by-product. Illustrative of the solvents which can be employed in our method we mention alkanoic acids, alkylformamides, alkylacetamides, alkylsulfoxides, alkylureas, alkylphosphoramides, alkylpyrrolidinones, aldehydes, ketones and ethers.

Specific examples of solvents which can be employed in addition to water include dimethylformamide, diethylformamide, dimethylacetamide, dimethylsulfoxide, tetramethylurea, tetraethylurea, hexamethylphosphoramide, 1-methyl-2-pyrrolidione, 1-ethyl-2-pyrrolidinone, 1,4-dimethyl-2-pyrrolidinone, butyraldehyde, acetone, methylethylketone, diethylether, 1,4-dioxane, tetrahydrofuran and tetrahydropyran. Mixtures of oxygenated polar solvents can also be used. A preferred oxygenated polar solvent is dimethylsulfoxide. As highly preferred solvents in our method we mention alkanoic acids of from 1 to 16 carbon atoms, particularly those of 2 to 6 carbons, including formic acid, acetic acid, propionic acid, butanoic acid, isobutanoic acid, pentanoic acid, hexanoic acid, octanoic acid, decanoic acid, undecanoic acid, pentadecanoic acid and hexadecanoic acid. In general, any oxygenated polar organic solvent characterized above that is liquid under the processing conditions set forth above can be employed.

Representative of the acids prepared by the instant method, we mention by way of illustration acetic acid, propionic acid, n-butanoic acid, n-pentanoic acid, n-hexanoic acid, n-tetradecanoic acid, n-pentadecanoic acid and n-eicosanoic acid. Ammonium halides prepared by the method include, for example, ammonium chloride, ammonium bromide, ammonium iodide, and ammonium fluoride.

At the completion of the reaction, the carboxylic acid product can be recovered by cooling the reaction mixture and isolating the resulting solid by filtration or decantation in those instances where higher molecular weight carboxylic acids are produced. Alternatively, the product can be isolated by fractional distillation at atmospheric or below atmosphere pressure. The ammonium halide can likewise be recovered by heating the residue and recovering the halide by sublimation. The other coproduct, carbon dioxide can be recovered, if desired, in the course of the reaction or at the completion thereof, by scrubbing the exit gas with an amine base at room temperature and thereafter thermally decomposing the amine-carbon dioxide complex.

By the instant method, acylhydroximyl halides can be selectively converted to carboxylic acids in yields as high as 90 percent. The acids prepared according to this invention are useful as chemical intermediates for the preparation of detergents, emulsifiers, turbine oils, plasticizers, paints, anti-freezing agents and rubbers.

In order to more fully illustrate the nature of our invention and the manner of practicing the same, the following examples are presented.

EXAMPLE I

To a solution composed of 250 milliliters of concentrated HCl (7.1 moles) in 750 milliliters of acetic acid (13 moles) heated to 95° C., there was introduced 100 grams of 1-nitro-2-hexadecanone (0.35 mole). The resulting clear solution was maintained at 95° to 104° C. for 100 minutes. The mixture was thereafter allowed to cool to about 25° C. and crystallized solids weighing 75.5 grams after drying were recovered. The filtrate was further cooled to 0° C. for 1 hour and a second crop of crystallized solids weighing 14.2 grams was collected. Thereafter the filtrate was poured into 150 milliliters of water and a third crop of crystallized product weighing 9.68 grams was collected. A combined yield of 94 percent of theoretical was recovered and this product was identified as n-pentadecanoylhydroximyl chloride by infrared, proton nuclear magnetic resonance and elemental analysis.

A solution composed of 2.0 grams (0.006 mole) of n-pentadecanoylhydroximyl chloride and 100 milliliters of water was heated for 24 hours at 100° C. Thereafter, the solution was poured into 100 milliliters of ice water. The mixture was filtered, the recovered solids dried and weighed 1.32 grams (yield 83 percent). The product was identified as pentadecanoic acid by infrared analysis. A white solid was also recovered and was identified as ammonium chloride by infrared analysis.

EXAMPLE II

A solution composed of less than 9.0 grams of pentadecanoylhydroximyl chloride and 100 milliliters of 37 percent aqueous hydrogen chloride was heated for 24 hours at 121° C. After cooling the mixture to room temperature, the mixture was extracted with two 50 milliliter portions of diethylether, two 50 milliliter portions of chloroform and one 50 milliliter portion of n-hexane. The combined extracts were dried, the solvents evaporated and 6.3 grams of pentadecanoic acid were recovered.

EXAMPLE III

A solution composed of 4.0 grams (0.014 mole) of pentadecanoylhydroximyl chloride in 100 milliliters of water was heated for 24 hours at 100° C. Recovery of the solids by cooling, filtering and drying provided 3.0 grams (94 percent yield) of product identified by infrared to be pentadecanoic acid.

We claim:

1. A method of preparing a carboxylic acid which comprises heating an acylhydroximyl halide corresponding to the formula:

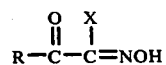

where R is an alkyl group of from 1 to 50 carbon atoms and where X is Cl, Br, I or F in the presence of at least greater than 5 moles of water per mole of said halide at a temperature of about 70° to 220° C.

2. A method according to claim 1 wherein said contacting is at a temperature of from about 90° to 170° C.

3. A method according to claim 1 wherein said heating is conducted in the presence of catalytic amounts of a mineral acid.

4. A method according to claim 3 wherein said mineral acid is hydrochloric acid, sulfuric acid, nitric acid or phosphoric acid.

5. A method according to claim 3 wherein said mineral acid is hydrochloric acid.

6. A method according to claim 1 where X is Cl.

7. A method according to claim 1 where R is 3 to 40 carbon atoms.

8. A method according to claim 1 wherein R is 5 to 30 carbon atoms.

9. A method according to claim 1 wherein said acylhydroximyl halide to pentadecanoylhydroximyl chloride.

10. A method according to claim 1 wherein said acylhydroximyl halide is heptadecanoylhydroximyl chloride.

11. A method according to claim 1 wherein said acylhydroximyl halide is pentadecanoylhydroximyl bromide.

12. A method according to claim 1 wherein said acylhydroximyl halide is pentadecanoylhydroximyl iodide.

13. A method according to claim 1 wherein said acylhydroximyl halide is pentadecanoylhydroximyl fluoride.

14. A method according to claim 1 wherein said carboxylic acid prepared is pentadecanoic acid.

15. A method according to claim 1 wherein said carboxylic acid prepared is acetic acid.

16. A method according to claim 1 wherein said heating is conducted in the presence of an oxygenated polar organic solvent.

17. A method according to claim 16 wherein said solvent is an alkanoic acid, an alkylformamide, an alkylacetamide, an alkylsulfoxide, an alkylurea, an alkylphosphoramide, an alkylpyrrolidinone, an aldehyde, a ketone or an ether.

18. A method according to claim 16 wherein said solvent is an alkanoic acid of from 1 to 16 carbon atoms.

19. A method according to claim 16 wherein said solvent is acetic acid.

20. A method according to claim 16 wherein said solvent is dimethylsulfoxide.

* * * * *